(12) United States Patent
Shirota et al.

(10) Patent No.: US 10,092,174 B2
(45) Date of Patent: Oct. 9, 2018

(54) ENDOSCOPE LIGHT SOURCE APPARATUS (71) Applicant: OLYMPUS CORPORATION, Tokyo (JP)

(72) Inventors: Yutaka Shirota, Hino (JP); Takahiro Masaki, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/238,285

(22) Filed: Aug. 16, 2016

(65) Prior Publication Data

US 2016/0353984 A1    Dec. 8, 2016

Related U.S. Application Data

(63) Continuation of application No. PCT/JP2015/055426, filed on Feb. 25, 2015.

(30) Foreign Application Priority Data

May 21, 2014    (JP) ................. 2014-105494

(51) Int. Cl.
*A61B 1/00* (2006.01)
*A61B 1/06* (2006.01)
(Continued)

(52) U.S. Cl.
CPC ............ *A61B 1/128* (2013.01); *A61B 1/0669* (2013.01); *F21V 29/503* (2015.01); *F21V 29/60* (2015.01);
(Continued)

(58) Field of Classification Search
CPC ........... A61B 1/12; A61B 1/121; A61B 1/126; A61B 1/127; A61B 1/128; A61B 1/00;
(Continued)

(56) References Cited

U.S. PATENT DOCUMENTS

2004/0133251 A1\* 7/2004 Altshuler ............ A61B 18/203
607/88
2008/0239070 A1\* 10/2008 Westwick ............ A61B 1/045
348/68

(Continued)

FOREIGN PATENT DOCUMENTS

JP    H01-183888 A    7/1989
JP    2001267773    9/2001
(Continued)

OTHER PUBLICATIONS

International Search Report dated May 26, 2015 issued is corresponding Japanese Patent Application No. PCT/JP2015/055426.
(Continued)

*Primary Examiner* — John P Leubecker
*Assistant Examiner* — William Chou
(74) *Attorney, Agent, or Firm* — Scully, Scott, Murphy & Presser, P.C.

(57)    ABSTRACT

A cooling device according to the invention includes: a first flow channel configured so that a coolant passes; a first heat receiving portion; a first heat radiating portion arranged in the first flow channel; a first heat transferring portion configured to transfer heat from the first heat receiving portion to the first heat radiating portion; a second flow channel configured so that the coolant passes; a second heat receiving portion; a second heat radiating portion arranged in the second flow channel; and a second heat transferring portion configured having a longer length than the first heat transferring portion and transferring heat from the second heat receiving portion to the second heat radiating portion. The second heat radiating portion is configured having a larger surface area than the first heat radiating portion.

3 Claims, 8 Drawing Sheets

(51) Int. Cl.
- *A61B 1/12* (2006.01)
- *G02B 23/24* (2006.01)
- *H01L 23/467* (2006.01)
- *H05K 7/20* (2006.01)
- *F21V 29/60* (2015.01)
- *F21V 29/503* (2015.01)
- *F21V 29/67* (2015.01)

(52) U.S. Cl.
CPC ............ *F21V 29/673* (2015.01); *G02B 23/24* (2013.01); *G02B 23/2476* (2013.01); *H01L 23/467* (2013.01); *H05K 7/20* (2013.01); *A61B 1/0684* (2013.01); *H01L 2924/0002* (2013.01)

(58) Field of Classification Search
CPC ..... A61B 1/012; A61B 1/015; A61B 1/00112; A61B 1/00119; A61B 1/00121; A61B 1/00128; A61B 1/00062; A61B 1/06; A61B 1/0661; A61B 1/0669
USPC ....... 600/102, 103, 109, 132, 133, 152, 156, 600/159, 160, 169, 178; 348/45, 65
See application file for complete search history.

(56) References Cited

U.S. PATENT DOCUMENTS

2009/0076329 A1* 3/2009 Su .................. A61B 1/0008 600/134
2015/0080933 A1* 3/2015 Igov ............... A61B 17/320016 606/190

FOREIGN PATENT DOCUMENTS

JP 2013215435 10/2013
JP 2014045820 3/2014

OTHER PUBLICATIONS

Japanese Office Action dated Feb. 2, 2016 issued is corresponding Japanese Patent Application No. 2015-550512.
Extended Supplementary European Search Report dated Oct. 10, 2017 in European Patent Application No. 15 79 6597.1.

* cited by examiner

FIG. 10 ptureETED# ENDOSCOPE LIGHT SOURCE APPARATUS

CROSS REFERENCE TO RELATED APPLICATION

This application is a continuation application of PCT/JP2015/055426 filed on Feb. 25, 2015 and claims benefit of Japanese Application No. 2014-105494 filed in Japan on May 21, 2014, the entire contents of which are incorporated herein by this reference.

BACKGROUND OF THE INVENTION

1. Field of the Invention

The present invention relates to a cooling device for cooling a plurality of heat generating portions, and an endoscope light source apparatus.

2. Description of the Related Art

For example, as disclosed in Japanese Patent Application Laid-Open Publication No. 2013-215435, some endoscope light source apparatuses are known which are provided with a plurality of solid light emitting devices such as LEDs and laser diodes.

Since solid light emitting devices generate heat when driven, it is necessary to provide a cooling device for cooling the solid light emitting devices when the solid light emitting devices are used as a light source for an endoscope light source apparatus. As the cooling device for cooling the solid light emitting devices, a configuration is conceivable in which, for example, a heat radiating portion which is a heat sink is arranged in a flow channel through which air as a coolant flows, and heat generated by the solid light emitting devices is transferred to the heat radiating portion by a heat transferring portion which is, for example, a heat pipe.

SUMMARY OF THE INVENTION

A cooling device according to an aspect of the present invention includes: a first flow channel configured so that a coolant passes; a first heat receiving portion configured so that heat generated by a first heat generating portion, between the heat generated by the first heat generating portion and heat generated by a second heat generating portion, is transferred, the first and second heat generating portions being arranged along one side surface of the first flow channel outside the first flow channel; a first heat radiating portion arranged in the first flow channel; a first heat transferring portion configured to connect the first heat receiving portion and the first heat radiating portion and transfer heat from the first heat receiving portion to the first heat radiating portion; a second flow channel configured so that the coolant passes, the second flow channel being provided with the first flow channel sandwiched between the one side surface and the second flow channel; a second heat receiving portion configured so that the heat generated by the second heat generating portion is transferred; a second heat radiating portion arranged in the second flow channel; and a second heat transferring portion configured having a longer length than the first heat transferring portion and configured to connect the second heat receiving portion and the second heat radiating portion and transfer heat from the second heat receiving portion to the second heat radiating portion. The second heat radiating portion is configured having a larger surface area than the first heat radiating portion.

Further, an endoscope light source apparatus according to an aspect of the present invention includes a plurality of solid light emitting devices as the first and second heat generating portions, and the cooling device described above.

DETAILED DESCRIPTION OF THE PREFERRED EMBODIMENTS

Preferred embodiments of the present invention will be described below with reference to drawings. Note that, in each drawing used in description below, a different reduced scale is used for each component so that the component is shown in a size recognizable on the drawing, and the present invention is not limited only to the number of components, shapes of the components, a ratio of sizes of the components and relative positional relationships among the respective components shown in the drawings.

First Embodiment

An endoscope light source apparatus 1 of the present embodiment is an apparatus that emits light for illuminating a target observed by an endoscope 100. The endoscope 100 has a configuration in which an image of a predetermined site to be observed in a subject such as a human body or a structure is optically picked up, and the image is outputted to a display apparatus not shown. Since the configuration of the endoscope 100 is well known, description of the configuration will be omitted.

Figure 1:
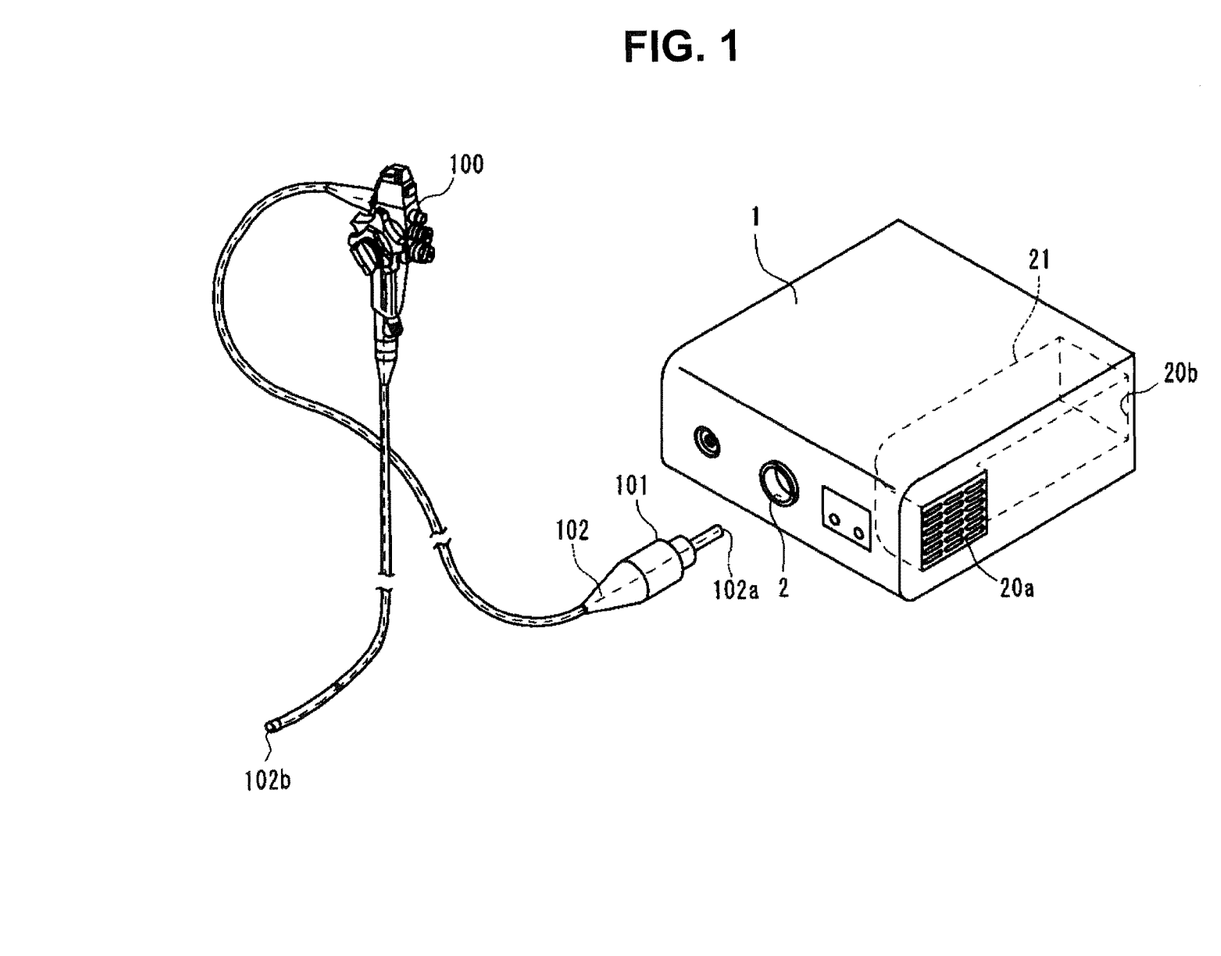
FIG. 1 is a perspective view of an endoscope light source apparatus.

As shown in FIG. 1, the endoscope light source apparatus 1 has a connector portion 2 to which a plug portion 101 provided on the endoscope 100 is connected. At the plug portion 101, one end 102a of an optical fiber cable 102 inserted through the endoscope 100 is arranged. Light caused to be incident on the one end 102a of the optical fiber cable 102 is emitted from the other end 102b toward an object of the endoscope 100.

The endoscope light source apparatus 1 has a plurality of solid light emitting devices as described later and has a configuration in which light emitted from the solid light emitting devices is caused to be incident on the one end 102a of the optical fiber cable 102 connected to the connector portion 2. The endoscope light source apparatus 1 is provided with a cooling device 20 for cooling the solid light emitting devices (not shown in FIG. 1). An intake port 20a which is an opening for introducing air, which is a coolant, into a flow channel 21 provided in the cooling device 20, and an exhaust port 20b which is an opening for discharging air from the flow channel 21 are provided on an outer surface of the endoscope light source apparatus 1. That is, the flow channel 21 is a tubular part configured so that air, which is a coolant, passes through.

Note that, though the intake port 20a and the exhaust port 20b are provided on a side surface and a back surface of the endoscope light source apparatus 1, respectively, in the shown embodiment, positions where the intake port 20a and the exhaust port 20b are provided are not limited to the present embodiment. For example, the intake port 20a and the exhaust port 20b only have to be provided on any of a front surface, back surface, top surface, bottom surface and side surface of the endoscope light source apparatus 1. Further, the intake port 20a and the exhaust port 20b may be provided on a same surface of the endoscope light source apparatus 1.

Figure 2:
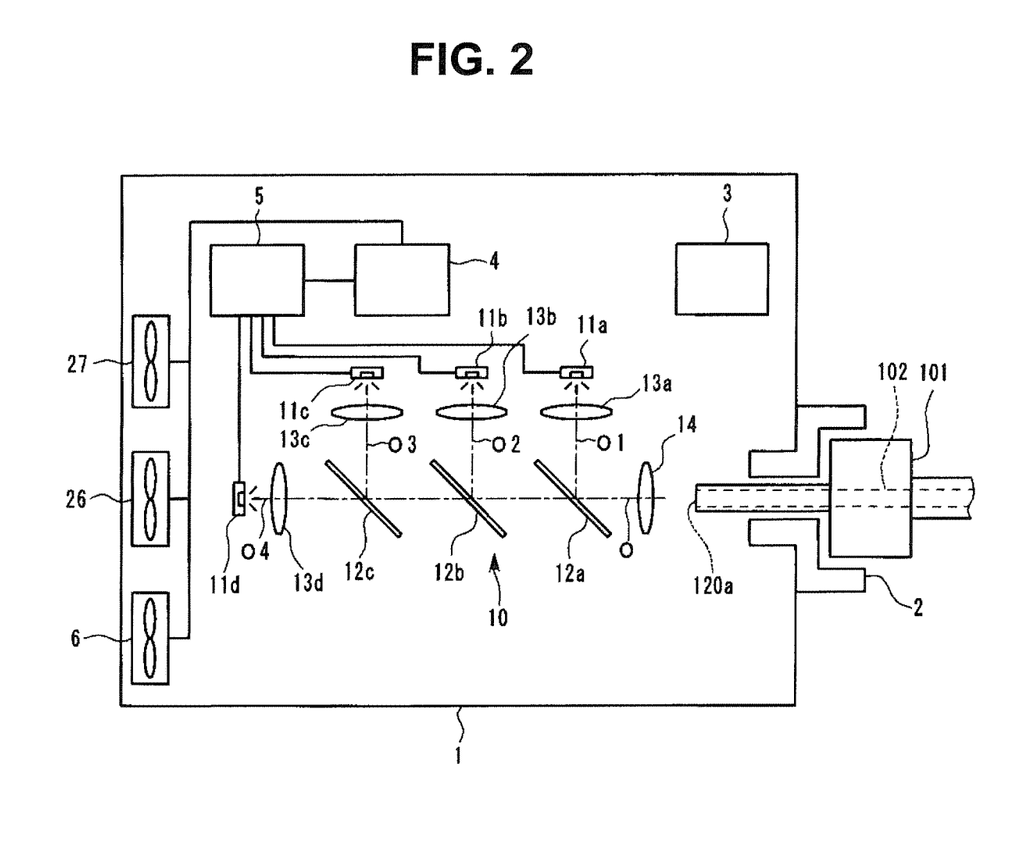
FIG. 2 is a diagram for illustrating electrical and optical configurations of the endoscope light source apparatus.

FIG. 2 is a diagram showing electrical and optical configurations of the endoscope light source apparatus 1. As shown in FIG. 2, the endoscope light source apparatus 1 is provided with an illuminating light emission device 10, a power source portion 3, a control portion 4, a light source driving portion 5, a housing inside cooling fan 6 and light source cooling fans 26, 27.

The power source portion 3 is a device configured to supply power for driving each part constituting the endoscope light source apparatus 1. The control portion 4 is configured having a central processing unit (CPU), a storage device (RAM), an auxiliary storage device, input/output devices and the like, and the control portion 4 is a device configured to control operation of the endoscope light source apparatus 1 based on a predetermined program. The light source driving portion 5 is a device having an electrical circuit configured to drive the solid light emitting devices to be described later, in response to an instruction from the control portion 4.

The illuminating light emission device 10 of the present embodiment is provided with four solid light emitting devices 11a, 11b, 11c, 11d. Each of the individual solid light emitting devices 11a, 11b, 11c, 11d may be either a laser diode or a light emitting diode (LED). Further, a wavelength of light emitted from each of the individual solid light emitting devices 11a, 11b, 11c, 11d is not especially limited. The solid light emitting devices 11a, 11b, 11c, 11d are electrically connected to the light source driving portion 5 and generate light in response to an electrical signal outputted from the light source driving portion 5. Further, strength of the light emitted from the solid light emitting devices 11a, 11b, 11c, 11d changes according to the electrical signal outputted from the light source driving portion 5.

In the present embodiment, as an example, the four solid light emitting devices 11a, 11b, 11c, 11d are LEDs each of which emits light of a predetermined wavelength region with a different wavelength as its center.

Lights emitted from the solid light emitting devices 11a, 11b, 11c, 11d are caused to be parallel lights by collimator lenses 13a, 13b, 13c, 13d, and, after that, guided to a condensing lens 14 by dichroic mirrors 12a, 12b, 12c. The condensing lens 14 condenses the lights emitted from the four solid light emitting devices 11a, 11b, 11c, 11d to the one end 102a of the optical fiber cable 102 which is located at the connector portion 2.

More specifically, in the present embodiment, when an axis passing through a center of the condensing lens 14 is assumed to be an optical axis O, one solid light emitting device 11d is arranged on the optical axis O, and the other three solid light emitting devices 11a, 11b, 11c are arranged at positions deviated from the optical axis O. In other words, the optical axis O can be said to be a central axis of light emitted from the illuminating light emission device 10.

When central axes of the lights emitted from the solid light emitting devices 11a, 11b, 11c, 11d are referred to as axes O1, O2, O3, O4, respectively, the axis O4 is parallel to the optical axis O.

On the other hand, the three solid light emitting devices 11a, 11b, 11c are arranged so that the axes O1, O2, O3 are orthogonal to the optical axis O on a same plane that includes the optical axis O. Further, on the same plane that includes the optical axis O, all of the solid light emitting devices 11a, 11b, 11c are arranged on a same side relative to the optical axis O (in FIG. 2, a lower side).

The collimator lenses 13a, 13b, 13c, 13d are arranged in front of the solid light emitting devices 11a, 11b, 11c, 11d, respectively, and emit the lights from the solid light emitting devices 11a, 11b, 11c, 11d as parallel lights.

In front of the three collimator lenses 13a, 13b, 13c, the dichroic mirrors 12a, 12b, 12c are provided. The dichroic mirrors 12a, 12b, 12c are arranged along the optical axis O. The dichroic mirrors 12a, 12b, 12c are arranged so that reflection planes are orthogonal to a plane that includes the optical axis O and the axes O1, O2, O3, and the reflection planes are inclined by 45 degrees relative to the optical axis O on the plane.

The reflection plane of the dichroic mirror 12a reflects light of a predetermined wavelength range which includes a wavelength of the light emitted from the solid light emitting device 11a and transmits lights of other wavelength ranges. The reflection plane of the dichroic mirror 12b reflects light of a predetermined wavelength range that includes a wavelength of the light emitted from the solid light emitting device 11b and transmits lights of other wavelength ranges. The reflection plane of the dichroic mirror 12c reflects light of a predetermined wavelength range that includes a wavelength of the light emitted from the solid light emitting device 11c and transmits lights of other wavelength ranges.

The parallel lights emitted from the collimator lenses 13a, 13b, 13c and reflected by the dichroic mirrors 12a, 12b, 12c are combined with light emitted from the collimator lens 13d and caused to be incident on the condensing lens 14.

In the illuminating light emission device 10 having a configuration as described above, the four solid light emitting devices 11a, 11b, 11c, 11d are arranged so that central axes of the lights emitted from the respective solid light emitting devices 11a, 11b, 11c, 11d are located on a same plane. The four solid light emitting devices 11a, 11b, 11c, 11d can be said to be arranged in that order in a predetermined direction along the optical axis O. Further, the four solid light emitting devices 11a, 11b, 11c, 11d are arranged so as not to be mutually overlapped in a direction orthogonal to the optical axis O.

Note that the number of solid light emitting devices the illuminating light emission device 10 is provided with is not limited to four, and any number equal to or larger than two is possible.

The housing inside cooling fan 6 is an electric fan configured to discharge air in a housing of the endoscope light source apparatus 1. The number of revolutions of the housing inside cooling fan 6 is detected by the control portion 4. The control portion 4 can cause the number of revolutions of the housing inside cooling fan 6 to change. Note that a form is also possible in which a plurality of housing inside cooling fans 6 are provided.

The light source cooling fans 26, 27 are electric fans provided in the cooling device 20 to be described later. The number of revolutions of the light source cooling fans 26, 27 is detected by the control portion 4. The control portion 4 can cause the number of revolutions of the light source cooling fans 26, 27 to change. Note that a form is also possible in which two or more light source cooling fans are provided.

Figure 3:
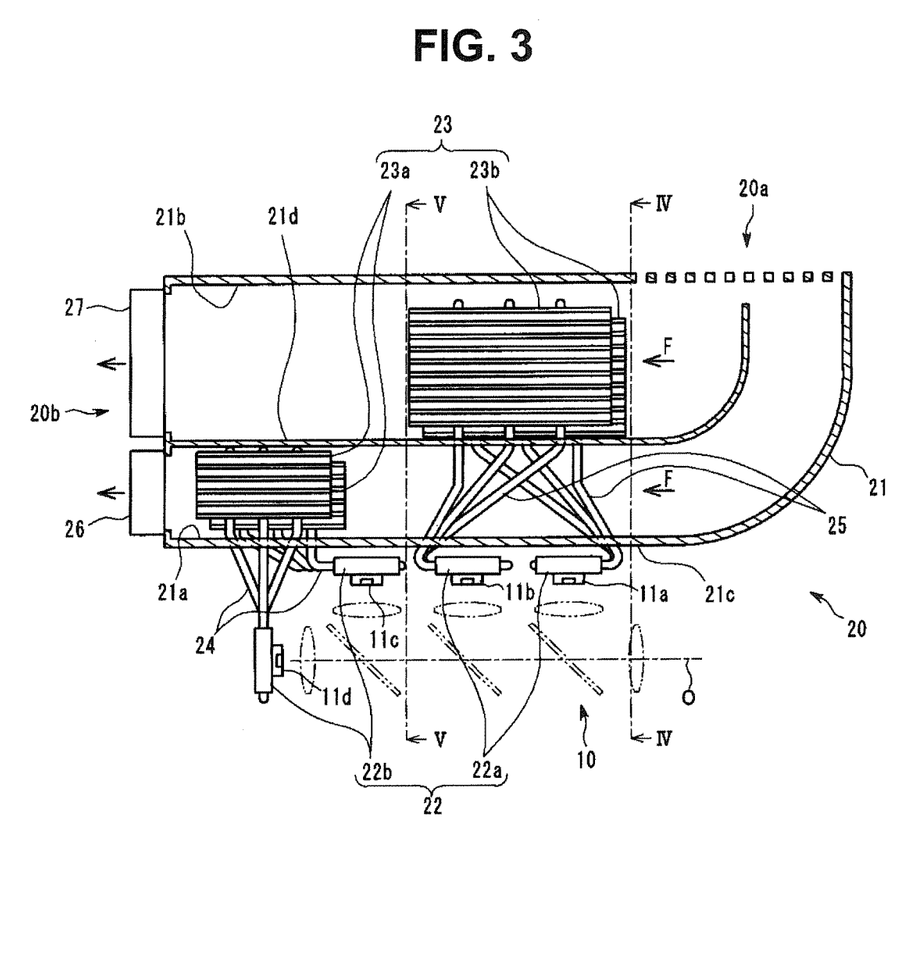
FIG. 3 is a diagram for illustrating a configuration of a cooling device.

FIG. 3 is a diagram showing a configuration of the cooling device 20. The cooling device 20 is a device configured to cool the solid light emitting devices 11a, 11b, 11c, 11d which are heat generating portions the illuminating light emission device 10 is provided with. The cooling device 20 is provided with the flow channel 21, heat receiving portions 22, heat radiating portions 23 and heat transferring portions 24.

The flow channel 21 is a part through which air, which is a coolant, passes. The flow channel 21 has a section extending in the direction along the optical axis O. That is, the flow channel 21 has a section through which air, which is a coolant, is caused to flow, along a direction of arrangement of the solid light emitting devices 11a, 11b, 11c, 11d. One end of the flow channel 21 is connected to the intake port 20a provided on the housing, and the other end of the flow channel 21 is connected to the exhaust port 20b provided on the housing. In the flow channel 21, the air, which is a coolant, flows in a direction from the intake port 20a toward the exhaust port 20b. That is, in the flow channel 21, a direction approaching the intake port 20a is an upstream side of air flow in the flow channel 21, and a direction approaching the exhaust port 20b is a downstream side.

More specifically, the flow channel 21 extends along the direction of arrangement of the three solid light emitting devices 11a, 11b, 11c in proximity to a back surface side of the three solid light emitting devices 11a, 11b, 11c. Here, back surfaces of the three solid light emitting devices 11a, 11b, 11c are surfaces facing a direction opposite to surfaces from which their respective lights are emitted. That is, the three solid light emitting devices 11a, 11b, 11c are located between the flow channel 21 and the optical axis O.

In other words, the four solid light emitting devices 11a, 11b, 11c, 11d, which are a plurality of heat generating portions arranged along the optical axis O are arranged in that order along a side surface 21c of the flow channel 21 in a direction in which the air which is a coolant flows in the flow channel 21. In FIG. 3, the direction in which the air which is a coolant flows in the flow channel 21 is indicated by an arrow F.

Figure 4:
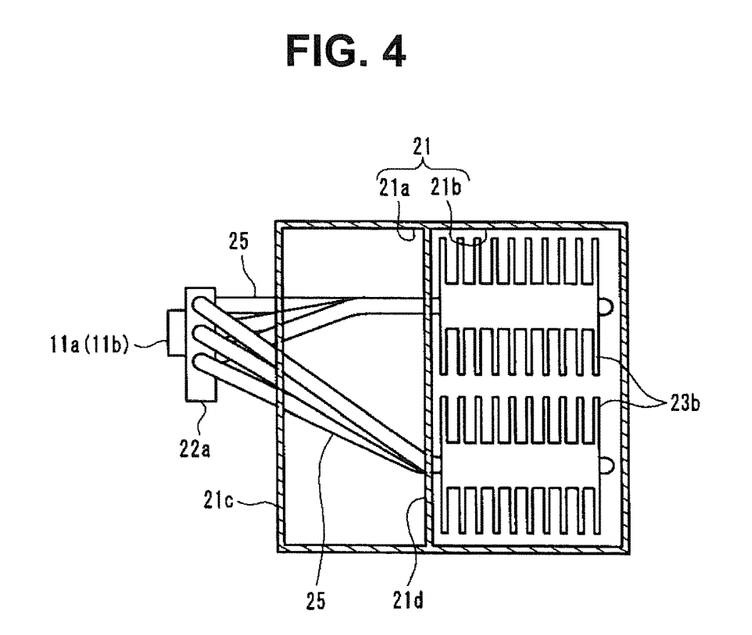
FIG. 4 is a IV-IV cross-sectional view of FIG. 3.
Figure 5:
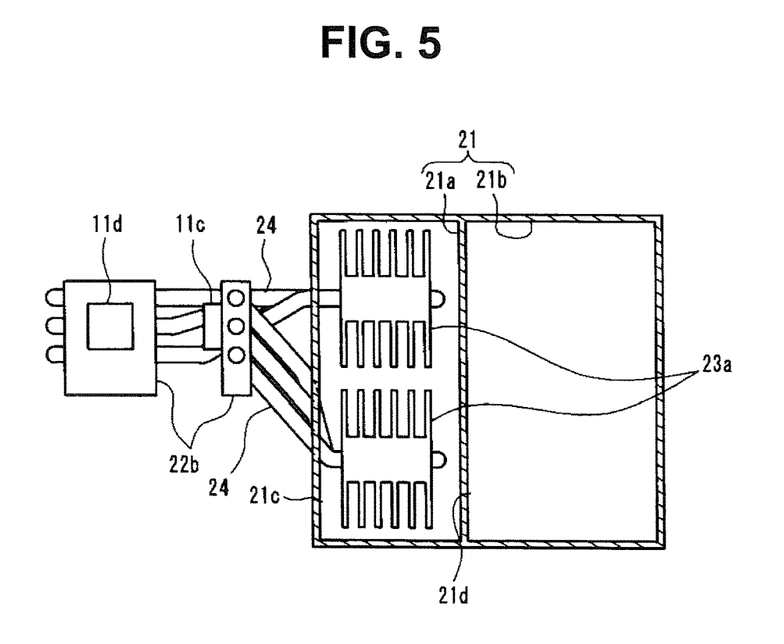
FIG. 5 is a V-V cross-sectional view of FIG. 3.

As shown in FIGS. 3 to 5, the flow channel 21 is divided into two of a first flow channel 21a and a second flow channel 21b. In the present embodiment, the first flow channel 21a and the second flow channel 21b, which are the two flow channels, are formed by arranging a partition plate 21d in the flow channel 21, as an example. Note that a form is also possible in which the first flow channel 21a and the second flow channel 21b are formed with separate members, respectively. Further, though the first flow channel 21a and the second flow channel 21b of the present embodiment have rectangular cross-sectional shapes as shown in FIGS. 4 and 5, the cross-sectional shapes of the first flow channel 21a and the second flow channel 21b may be other shapes such as a circle and a semicircle.

The first flow channel 21a is arranged in close proximity to the side surface 21c. Further, the second flow channel 21b is arranged so that the first flow channel 21a is sandwiched between the side surface 21c and the second flow channel 21b. That is, the flow channel 21 is divided into the first flow channel 21a in close proximity to the four solid light emitting devices 11a, 11b, 11c, 11d, which are a plurality of heat generating portions arranged along the optical axis O, and the second flow channel 21b arranged at a position further away from the four solid light emitting devices 11a, 11b, 11c, 11d than the first flow channel 21a. The first flow channel 21a is arranged between the second flow channel 21b and the four solid light emitting devices 11a, 11b, 11c, 11d.

The plurality of heat receiving portions 22 are provided in close proximity to the four solid light emitting devices 11a, 11b, 11c, 11d, which are a plurality of heat generating portions, individually. The plurality of heat receiving portions 22 are members through which heat generated by the solid light emitting devices 11a, 11b, 11c, 11d is transferred. Note that the heat receiving portions 22 and the solid light emitting devices 11a, 11b, 11c, 11d may be in a form of being mutually in contact or may be in a form of mutually facing with a heat transferring member sandwiched between the heat receiving portions 22 and the solid light emitting devices 11a, 11b, 11c, 11d. Note that, though the individual heat receiving portions 22 are arranged on the back surface side of the solid light emitting devices 11a, 11b, 11c, 11d in the shown present embodiment, the form of the heat receiving portions 22 is not especially limited if the form is such that light emitted from the solid light emitting devices 11a, 11b, 11c, 11d is not blocked.

Here, two heat receiving portions 22 provided corresponding to the two solid light emitting devices 11a and 11b located on the upstream side of the air flow in the flow channel 21, among the four solid light emitting devices 11a, 11b, 11c, 11d, which are a plurality of heat generating portions, will be referred to as upstream-side heat receiving portions 22a. Further, among the solid light emitting devices 11a, 11b, 11c, 11d, which are a plurality of heat generating portions, those excluding the upstream-side heat receiving portions will be referred to as downstream-side heat receiving portions 22b.

The plurality of heat radiating portions 23 are heat sinks arranged in the flow channel 21. In the present embodiment, the cooling device 20 has four heat radiating portions 23, the number four being the same as the number of heat receiving portions 22. The four heat radiating portions 23 include two first heat radiating portions 23a arranged in the first flow channel 21a and two second heat radiating portions 23b arranged in the second flow channel 21b.

In the present embodiment, the two first heat radiating portions 23a are connected to the two downstream-side heat receiving portions 22b, respectively, via the heat transferring portions 24 which are heat transfer means. In the present embodiment, the heat transferring portions 24 are heat pipes as an example. The form of the heat transferring portions 24 is not limited to the form of heat pipes. Any member that efficiently transfers heat is possible. That is, the two first heat radiating portions 23a are provided corresponding to the two solid light emitting devices 11c and 11d located on a downstream side of the air flow in the flow channel 21. Note that the number of the heat transferring portions 24 connecting the first heat radiating portions 23a and the downstream-side heat receiving portions 22b is appropriately determined according to an amount of heat to be transferred and may be one or plural.

As shown in FIG. 5, the two first heat radiating portions 23a are arranged so as not to be overlapped with each other in the first flow channel 21a when seen from a direction along the air flow direction. Further, as shown in FIG. 3, the two first heat radiating portions 23a are arranged so that at least parts of the first heat radiating portions 23a are overlapped with each other when seen from a direction orthogonal to the air flow direction in the first flow channel 21a.

Further, in the present embodiment, the two second heat radiating portions 23b are connected to the two upstream-side heat receiving portions 22a, respectively, via heat transferring portions 25 which are heat transfer means. In the present embodiment, the heat transferring portions 25 are heat pipes as an example. The form of the heat transferring portions 25 is not limited to the form of heat pipes. Any member that efficiently transfers heat is possible. That is, the two second heat radiating portions 23b are provided corresponding to the two solid light emitting devices 11a and 11b located on the upstream side of the air flow in the flow channel 21. Note that the number of the heat transferring portions 25 connecting the second heat radiating portions 23b and the upstream-side heat receiving portions 22a is appropriately determined according to an amount of heat to be transferred and may be one or plural.

As shown in FIG. 4, the two second heat radiating portions 23b are arranged so as not to be overlapped with each other in the second flow channel 21b when seen from the direction along the air flow direction. Further, as shown in FIG. 3, the two second heat radiating portions 23b are arranged so that at least parts of the second heat radiating portions 23b are overlapped with each other when seen from the direction orthogonal to the air flow direction in the second flow channel 21b.

Further, as shown in FIGS. 3 and 4, the two second heat radiating portions 23b have a surface area larger than that of the two first heat radiating portions 23a. The heat transferring portions 25 connecting the second heat radiating portions 23b and the upstream-side heat receiving portions 22a are arranged so as to pass through the first flow channel 21a.

As described before, the light source apparatus 1 is provided with the light source cooling fans 26 and 27 which are two electric fans. The light source cooling fans 26 and 27 are for causing air, which is a coolant, to flow in the first flow channel 21a and the second flow channel 21b, respectively, at a predetermined flow rate.

In the present embodiment, the light source cooling fans 26 and 27 are arranged in close proximity to the exhaust port 20b. That is, the light source cooling fans 26 and 27 are arranged on a downstream side of the first heat radiating portions 23a and the second heat radiating portions 23b. Further, in the present embodiment, the light source cooling fans 26 and 27 are axial-flow fans as an example.

Figure 6:
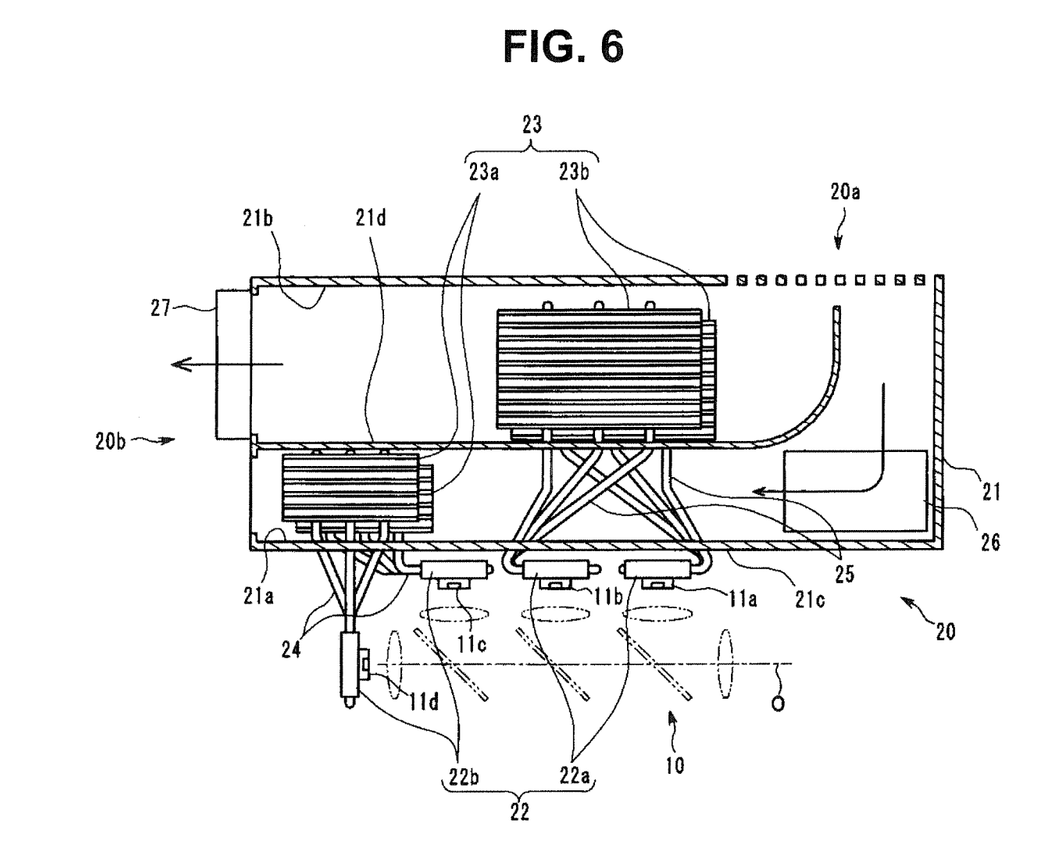
FIG. 6 is a diagram showing a modification of the cooling device.

Note that, the form and arrangement positions of the light source cooling fans 26 and 27 are not especially limited if it is possible to cause air to flow in the first flow channel 21a and the second flow channel 21b at a predetermined flow rate. For example, a form is also possible in which at least either the light source cooling fan 26 or the light source cooling fan 27 is arranged in close proximity to the intake port 20a. Further, at least either the light source cooling fan 26 or the light source cooling fan 27 may be a centrifugal fan (blower fan). In a modification shown in FIG. 6, the light source cooling fan 26 provided in the first flow channel 21a is a blower fan and is arranged on an upstream side of the first heat radiating portions 23a.

In the cooling device 20 configured as described above, by causing the light source cooling fans 26 and 27 to operate and causing air to flow in the first flow channel 21a and the second flow channel 21b at a predetermined flow rate, heat transferred from the solid light emitting devices 11a, 11b, 11c, 11d to the heat receiving portions 22 can be radiated at the heat radiating portions 23. That is, the cooling device 20 can cool the solid light emitting devices 11a, 11b, 11c, 11d.

Here, in the cooling device 20 of the present embodiment, the flow channel 21 through which air, which is a coolant, is caused to flow is divided into two of the first flow channel 21a in close proximity to the solid light emitting devices 11a, 11b, 11c, 11d which are heat generating portions and the second flow channel 21b provided on an opposite side of the solid light emitting devices 11a, 11b, 11c, 11d, with the first flow channel 21a between the solid light emitting devices 11a, 11b, 11c, 11d and the second flow channel 21b.

The two first heat radiating portions 23a arranged in the first flow channel 21a are arranged so as not to be overlapped with each other when seen from the direction along the air flow direction and arranged close to each other in the direction orthogonal to the flow direction. Further, the two second heat radiating portions 23b arranged in the second flow channel 21b are arranged so as not to be overlapped with each other when seen from the direction along the air flow direction and arranged close to each other in the direction orthogonal to the flow direction. By the configuration, air at same temperature as room temperature, which is acquired from the intake port 20a, is applied to all the first heat radiating portions 23a and the second heat radiating portions 23b. Therefore, it is possible to reduce the surface area of the first heat radiating portions 23a and the second heat radiating portions 23b and downsize the cooling device 20.

Especially, as for the two first heat radiating portions 23a arranged in the first flow channel 21a in close proximity to the solid light emitting devices 11c and 11d, it is possible to shorten length of the heat transferring portions 24 and decrease thermal resistance of the heat transferring portions 24, and, therefore, it is possible to reduce the surface area. Similarly, it is possible to reduce a cross section of the first flow channel 21a and downsize the light source cooling fan 26, and, therefore, it is possible to downsize the cooling device 1.

Further, as for the second heat radiating portions 23b located at positions relatively far away from the solid light emitting devices 11a and 11b, it is possible to shorten length of the heat transferring portions 25 by routing the heat transferring portions 25 so as to pass through the first flow channel 21a. Because the heat transferring portions 25 are longer compared with the heat transferring portions 24, it is necessary to cause the surface area of the second heat radiating portions 23b to be larger than that of the first heat radiating portions 23a. However, by routing the heat transferring portions 25 by a shortest distance, it is possible to minimize an amount of increase in the surface area of the second heat radiating portions 23b.

As described above, according to the present invention, it is possible to downsize a cooling device having a plurality of heat radiating portions and heat transferring portions. Further, it is also possible to downsize the endoscope light source apparatus 1 provided with the cooling device 20 according to the present invention.

Note that, though the two first heat radiating portions 23a arranged in the first flow channel 21a are connected to the downstream-side heat receiving portions 22b via the heat transferring portions in the present embodiment, a form is also possible in which the two first heat radiating portions 23a arranged in the first flow channel 21a are connected to the upstream-side heat receiving portions 22a via the heat transferring portions. In this case, the two second heat radiating portions 23b arranged in the second flow channel 21b are connected to the downstream-side heat receiving portions 22b via the heat transferring portions.

Figure 7:
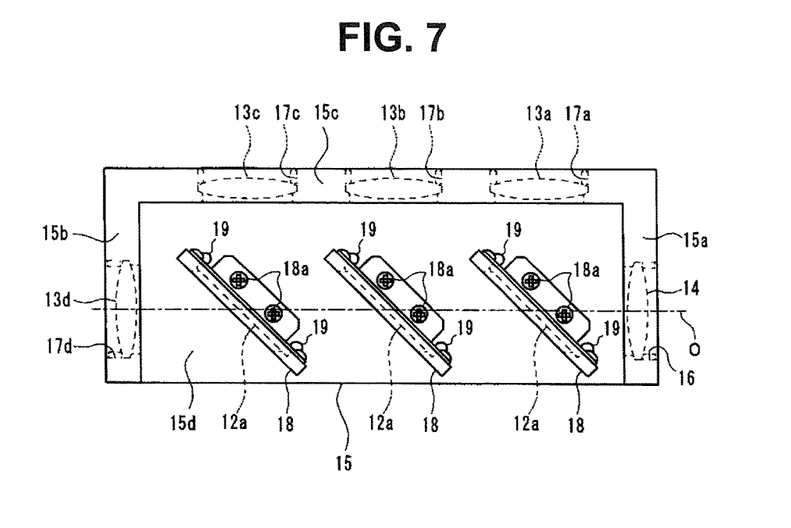
FIG. 7 is a diagram showing a configuration of an illuminating light emission device.

Next, description will be made on a configuration of holding the condensing lens 14, the dichroic mirrors 12a, 12b, 12c and the collimator lenses 13a, 13b, 13c, 13d in the illuminating light emission device 10.

As shown in FIG. 7, the condensing lens 14, the dichroic mirrors 12a, 12b, 12c and the collimator lenses 13a, 13b, 13c, 13d are fixed to a single holding frame 15.

The holding frame 15 includes a first wall surface 15a and a second wall surface 15b, which are flat-plate-shaped parts orthogonal to the optical axis O and separate from each other in the direction along the optical axis O; a third wall surface 15c which is a flat-plate-shaped part parallel to the optical axis O arranged between the first wall surface 15a and the second wall surface 15b; and a fourth wall surface 15d which is a flat-plate-shaped part parallel to the optical axis O and orthogonal to the third wall surface 15c arranged between the first wall surface 15a and the second wall surface 15b. That is, the holding frame 15 has a shape obtained by removing two adjacent side surfaces parallel to the optical axis O from a rectangular parallelepiped with the direction parallel to the optical axis O as its longitudinal direction.

A through hole 16 with the optical axis O as its center is formed in the first wall surface 15a. The condensing lens 14 is fixed in the through hole 16. The condensing lens 14 is positioned by being fitted into the through hole 16.

A through hole 17d with the optical axis O as its center is formed in the second wall surface 15b. The collimator lens 13d is fixed in the through hole 17d. The collimator lens 13d is positioned by being fitted into the through hole 17d.

Three through holes 17a, 17b, 17c with three axes orthogonal to the optical axis O and parallel to one another as their centers are formed in the third wall surface 15c. The collimator lenses 13a, 13b, 13c are fixed in the through holes 17a, 17b, 17c. The collimator lenses 13a, 13b, 13c are positioned by being fitted into the through holes 17a, 17b, 17c.

Three mirror holding frames 18 to be described later are fixed to the fourth wall surface 15d by screws 18a.

Figure 8:
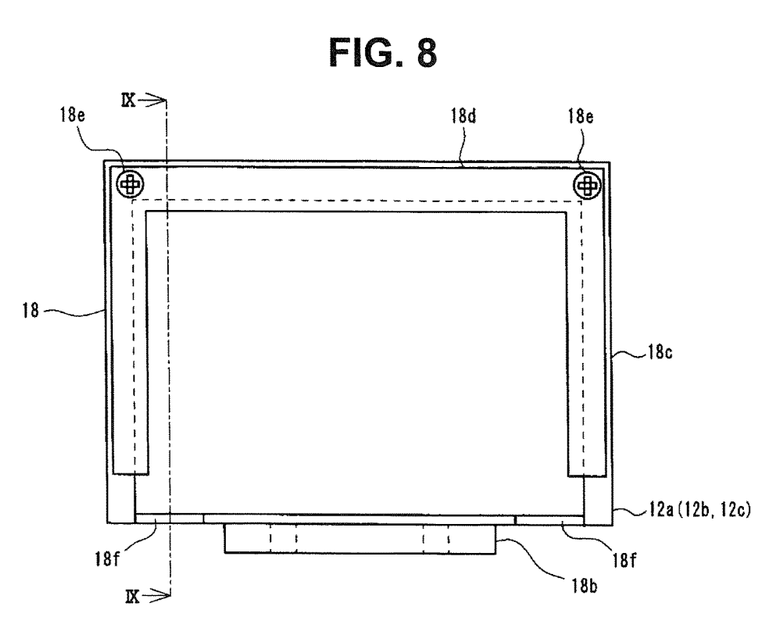
FIG. 8 is a front view of a mirror holding frame.
Figure 9:
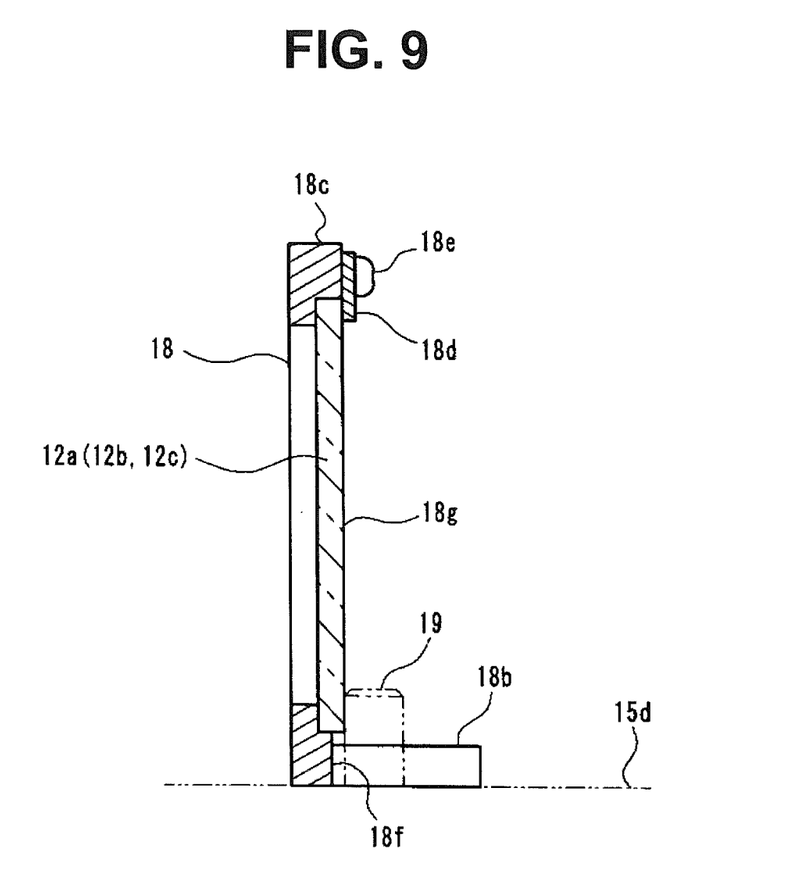
FIG. 9 is a IX-IX cross-sectional view of FIG. 8.

As shown in FIGS. 8 and 9, each mirror holding frame 18 is provided with a base 18b which is in contact with the fourth wall surface 15d, and a frame portion 18c which stands from the base 18a being orthogonal relative to the fourth wall surface 15d. The frame portion 18c is a rectangular frame-shaped part in which the dichroic mirror 12a (12b, 12c) is fitted. A mirror pressing member 18d is fixed to the frame portion 18c by screws 18e. The dichroic mirror 12a (12b, 12c) is fixed to the frame portion 18c in a state of being fitted in the frame portion 18c by the mirror pressing member 18d.

Notch portions 18f are formed on both end portions of a side on which the base 18b of the frame portion 18c is provided, that is, a side in close proximity to the fourth wall surface 15d. The notch portions 18f are provided so that pins 19 provided on the fourth wall surface 15d in a state of standing can come into contact with a reflection plane 18g of the dichroic mirror 12a (12b, 12c). As shown in FIG. 7, a pair of pins 19 is arranged for each of the dichroic mirrors 12a, 12b, 12c.

In a case of fixing the dichroic mirror 12a, 12b, 12c to the holding frame 15, the dichroic mirror 12a, 12b, 12c are fixed to the frame portions 18c with use of the mirror pressing members 18d and the screws 18e first. Then, the mirror holding frames 18 are fixed with use of the screws 18a while the reflection planes 18g of the dichroic mirror 12a, 12b, 12c are caused to be in contact with the pair of pins 19. By causing the reflection planes 18g of the dichroic mirror 12a, 12b, 12c to be in contact with the pair of pins 19 fixed to the fourth wall surface 15d of the holding frame 15 in this way, the dichroic mirror 12a, 12b, 12c are positioned.

As described above, in the present embodiment, the condensing lens 14, the dichroic mirrors 12a, 12b, 12c and the collimator lenses 13a, 13b, 13c, 13d, which are all optical members constituting the illuminating light emission device 10, are positioned on and fixed to the holding frame 15 which is a single member. Therefore, it becomes unnecessary to perform positioning work for the individual optical members, and assembly work for the illuminating light emission device 10 becomes easy.

Second Embodiment

A second embodiment of the present invention will be described below. Only points of difference from the first embodiment will be described below. Components similar to those of the first embodiment will be given same reference numerals, and description of the components will be appropriately omitted.

Figure 10:
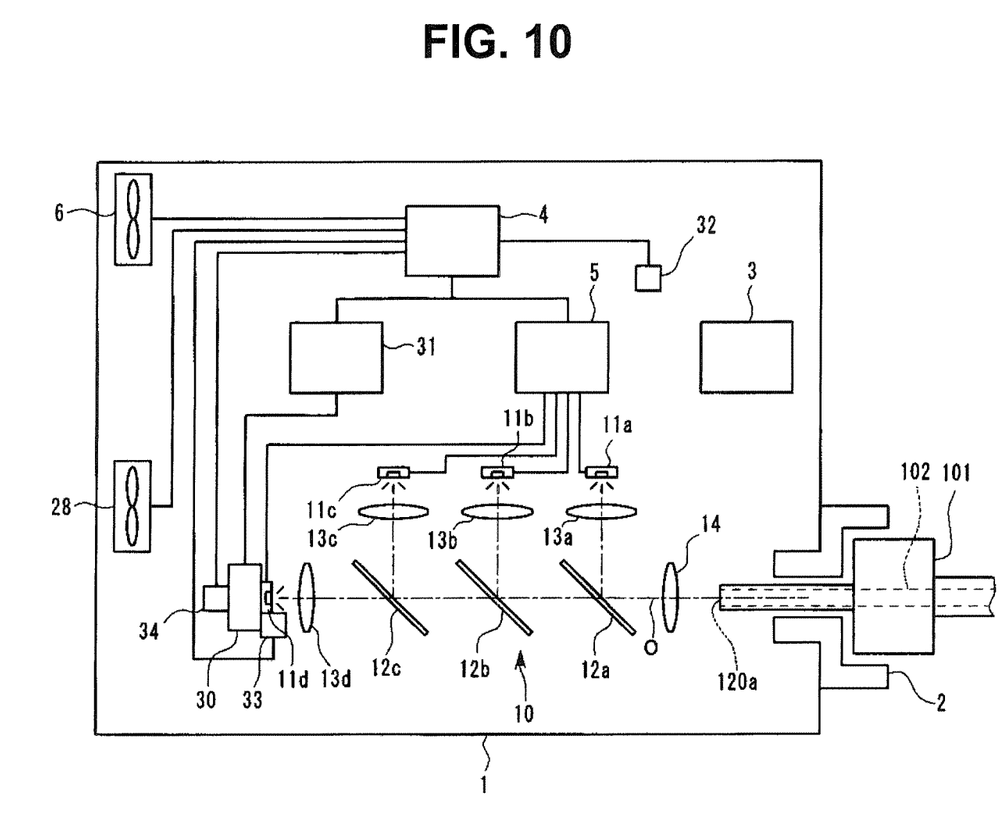
FIG. 10 is a diagram for illustrating a configuration of an endoscope light source apparatus 1 of a second embodiment.

An endoscope light source apparatus 1 of the present embodiment shown in FIG. 10 is different from the first embodiment in a point that the endoscope light source apparatus 1 is provided with a peltier element 30, and solid light emitting devices are cooled by the peltier element 30. In the endoscope light source apparatus 1 of the present embodiment, the peltier element 30 is arranged in close proximity to at least one of the solid light emitting devices 11a, 11b, 11c, 11d.

In the present embodiment, the peltier element 30 is provided in close proximity to the solid light emitting devices 11d as an example. Operation of the peltier element 30 is controlled by a peltier element driving portion 31. The peltier element driving portion 31 can detect whether there is a failure of the peltier element 30 or not.

Further, the endoscope light source apparatus 1 is provided with a housing inside temperature detecting portion 32 configured to detect temperature inside the housing, a solid light emitting device temperature detecting portion 33 configured to detect temperature of the solid light emitting device 11d, and a peltier element temperature detecting portion 34 configured to detect temperature of the peltier element 30. The housing inside temperature detecting portion 32, the solid light emitting device temperature detecting portion 33 and the peltier element temperature detecting portion 34 are electrically connected to the control portion 4.

Further, the endoscope light source apparatus 1 of the present embodiment is provided with a light source cooling fan 28 configured to cool the solid light emitting devices 11a, 11b, 11c, 11d and the housing inside cooling fan 6 configured to discharge air in the housing. The number of revolutions of the light source cooling fan 28 and the housing inside cooling fan 6 is detected by the control portion 4. Further, the control portion 4 can cause the number of revolutions of the light source cooling fan 28 and the housing inside cooling fan 6 to change.

The control portion 4 executes operation described below based on the number of revolutions of the light source cooling fan 28 and the housing inside cooling fan 6, output signals from the housing inside temperature detecting portion 32, the solid light emitting device temperature detecting portion 33 and the peltier element temperature detecting portion 34, and an output signal from the peltier element driving portion 31.

The control portion 4 controls the number of revolutions of the light source cooling fan 28 and the housing inside cooling fan 6 and operation of the peltier element 30 so that each of the temperature of the solid light emitting devices 11d and the temperature inside the housing is within a predetermined target temperature range.

Here, if the temperature of the solid light emitting device 11d continues exceeding the predetermined target temperature range even in a state in which cooling effect by the light source cooling fan 28 and the peltier element 30 is maximized, the control portion 4 stops driving of the solid light emitting devices 11a, 11b, 11c, 11d. Further, when the temperature of the peltier element 30 exceeds a predetermined temperature also, the control portion 4 stops driving of the solid light emitting devices 11a, 11b, 11c, 11d.

Further, if the temperature of the peltier element 30 is below the temperature inside the housing, the control portion 4 stops driving of the peltier element 30 until the temperature of the peltier element 30 exceeds the temperature inside the housing. This is because, when the temperature of the peltier element 30 is below the temperature inside the housing, dew condensation occurs.

If judging that the solid light emitting device temperature detecting portion 33 is under failure, the control portion 4 stops driving of the solid light emitting devices 11a, 11b, 11c, 11d. Further, if judging that the housing inside temperature detecting portion 32 is under failure, the control portion 4 maximizes the number of revolutions of the housing inside cooling fan 6.

If judging that the peltier element 30 and/or the peltier element temperature detecting portion 34 is under failure, the control portion 4 stops driving of the peltier element 30 and maximizes the number of revolutions of the light source cooling fan 28 and the housing inside cooling fan 6. Further, in this case, the control portion 4 decreases an amount of light of the solid light emitting devices 11a, 11b, 11c, 11d so that the solid light emitting devices 11a, 11b, 11c, 11d can be continuously driven only by cooling by the light source cooling fan 28 and the housing inside cooling fan 6. That is, even if the peltier element 30 has failed or it becomes impossible to detect the temperature of the peltier element 30 while the endoscope light source apparatus 1 is operating, emission of illuminating light is continued.

Thus, in the present embodiment, even if a failure of the peltier element 30 and/or the peltier element temperature detecting portion 34 occurs, it is possible to prevent a field of view of the endoscope 100 from being lost immediately, by decreasing the amount of illuminating light to cause emission of the illuminating light to be continued.

Note that the present invention is not limited to the embodiments described above and can be appropriately changed within a range not departing from the spirit or idea of the invention read from the Claims and the whole specification. A cooling device and an endoscope light source apparatus in which such changes have been made are also included within the technical scope of the present invention.

What is claimed is:

1. An endoscope light source apparatus comprising:
    a housing including a connector connected with an endoscope through which an optical fiber cable is inserted, the housing including a wall surface including an intake port;
    a first flow channel forming portion arranged in the housing, the first flow channel forming portion forming a first flow channel configured so that a first coolant passes from the intake port;
    a second flow channel forming portion arranged in the housing, the second flow channel forming portion forming a second flow channel configured such that a second coolant different from the first coolant passes from the intake port, the second flow channel being arranged adjacently and parallel to the first flow channel, the second flow channel being provided closer to the wall surface than the first flow channel;
    first and second light emitting devices arranged in the housing, the first and second light emitting devices emitting light to be incident on the optical fiber cable inserted through the endoscope, the first and second light emitting devices being arranged parallel to the first flow channel along one side surface of the first flow channel forming portion, the one side surface being on an opposite side of the second flow channel,
    a first heat pipe connected with the first light emitting device, the first heat pipe being configured to transfer the heat of the first light emitting device;
    a first heat sink connected to the first heat pipe, the first heat sink being arranged in the first flow channel, the first heat sink radiating heat transferred by the first heat pipe to the coolant that passes through the first flow channel;
    a second heat pipe connected with the second light emitting device, the second heat pipe being configured to transfer the heat of the second light emitting device, the second heat pipe having a length longer than a length of the first heat pipe, the second heat pipe passing between the intake port and the first heat sink in the first flow channel; and
    a second heat sink connected to the second heat pipe, the second heat sink being arranged in the second flow channel, the second heat sink radiating heat transferred by the second heat pipe to the coolant that passes through the second flow channel, the second heat pipe having a surface area larger than a surface area of the first heat sink.

2. The endoscope light source apparatus according to claim 1, wherein
    the one side surface of the first flow channel forming portion is a partition provided between the first and second light emitting devices and the wall surface of the housing; and
    the second flow channel forming portion is a partition provided between the wall surface of the housing and the first flow channel forming portion.

3. The endoscope light source apparatus according to claim 2, wherein the second heat sink is arranged at a position closer to the intake port with respect to the first heat sink in the second flow channel.

* * * * *